United States Patent [19]

Mioduski

[11] Patent Number: 4,644,955
[45] Date of Patent: * Feb. 24, 1987

[54] CIRCUIT APPARATUS AND METHOD FOR ELECTROTHERMAL TREATMENT OF CANCER EYE

[75] Inventor: Paul Mioduski, Tucson, Ariz.

[73] Assignee: RDM International, Inc., Phoenix, Ariz.

[*] Notice: The portion of the term of this patent subsequent to Jul. 30, 2002 has been disclaimed.

[21] Appl. No.: 708,007

[22] Filed: Mar. 4, 1985

Related U.S. Application Data

[63] Continuation of Ser. No. 453,811, Dec. 27, 1982, Pat. No. 4,531,524.

[51] Int. Cl.[4] .................................................. A61N 1/32
[52] U.S. Cl. ..................................... 128/422; 128/399; 128/800; 128/804; 128/303.13
[58] Field of Search ............ 128/422, 399, 736, 303.1, 128/800, 804, 419 R, 421, 303.13

[56] References Cited

U.S. PATENT DOCUMENTS

| 4,016,886 | 4/1977 | Doss et al. | 128/422 |
| 4,074,719 | 2/1978 | Semm | 128/303.1 |
| 4,124,030 | 11/1978 | Roberts | 128/422 |
| 4,189,685 | 2/1980 | Doss | 331/62 |
| 4,237,898 | 12/1980 | Whalley | 128/422 |
| 4,531,524 | 7/1985 | Mioduski | 128/422 |

Primary Examiner—Edward M. Coven
Attorney, Agent, or Firm—Cahill, Sutton & Thomas

[57] ABSTRACT

Circuitry for use in a hand-held electronic probe for passing high frequency current through malignant eye tissue of livestock or other tissue such as warts includes a thermistor in a probe tip that contacts the tissue, producing a voltage that controls a voltage controlled oscillator which drives an audio transducer. If, during treatment, the probe tip is held against the malignant tissue with sufficient force, the pitch of a sound emitted by the audio transducer steadily increases, indicating to the user that proper pressure is being maintained to ensure heating of the tissue to the desired treatment temperature. The circuitry then causes the transducer to emit periodic beeping signals which the user can count to ensure that the tissue is maintained in a desired elevated temperature range for a desired amount of time. Circuitry responsive to the temperature sensor varies the duty cycle of the high frequency current applied to the tissue to maintain the elevated temeperature thereof within a predetermined range. Initially, the high frequency current is applied at a substantially reduced duty cycle to prevent excessive temperature lag between the tissue and the probe tip to prevent initial temperature overshoot of the tissue before the thermistor and circuitry can respond to reduce the duty cycle.

4 Claims, 5 Drawing Figures

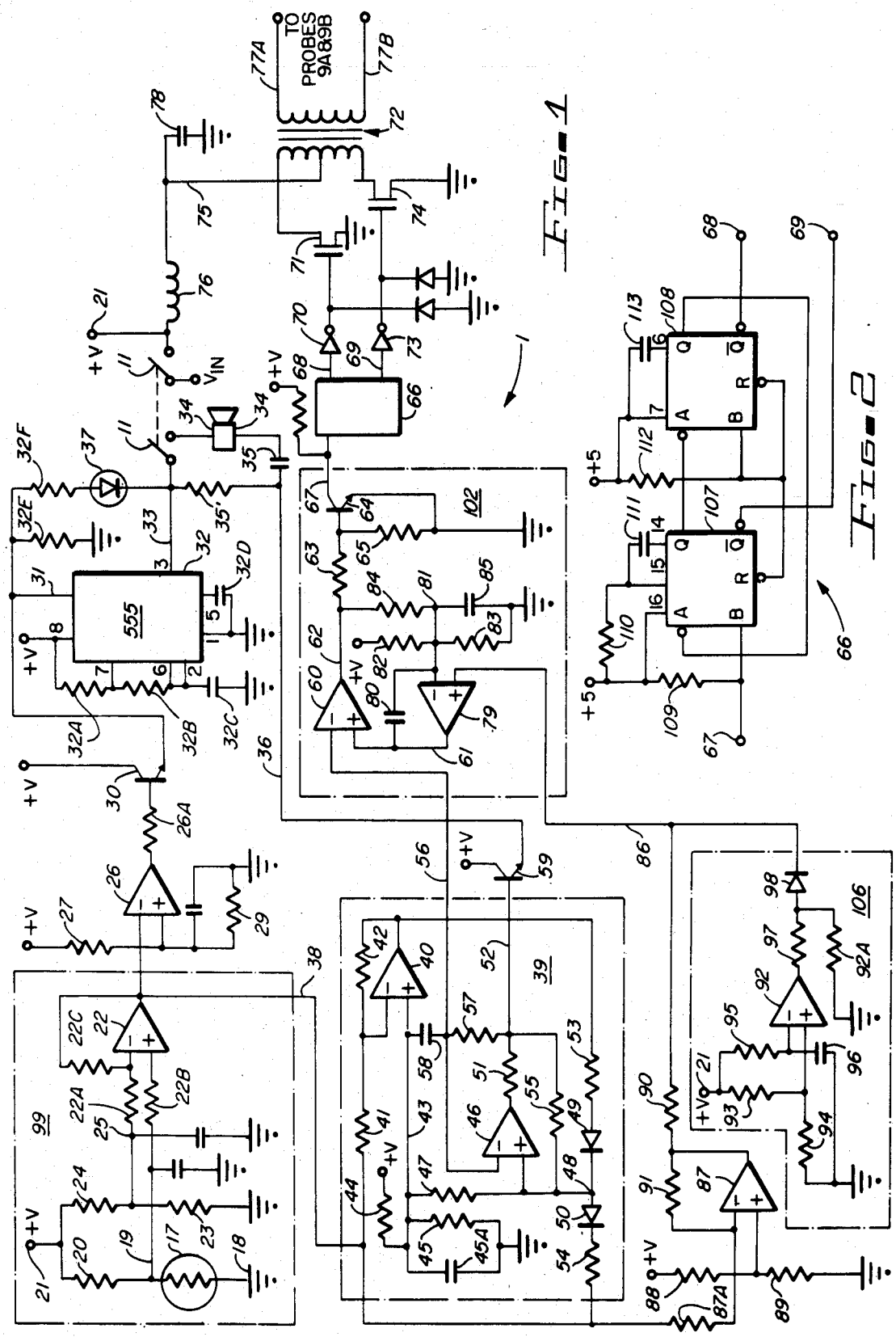

CIRCUIT APPARATUS AND METHOD FOR ELECTROTHERMAL TREATMENT OF CANCER EYE

This is a continuation of application Ser. No. 453,811, filed Dec. 27, 1982, now U.S. Pat. No. 4,531,524.

BACKGROUND OF THE INVENTION

The invention relates to apparatus and methods for treating malignant tissue known as "cancer eye" in the eyes of livestock by applying high frequency current, by means of spaced probes, to the malignant tissue to increase the temperature thereof to a level which is high enough to kill the malignant tissue but is low enough to avoid permanent damage to the adjacent healthy tissue.

Benign and malignant tumors of the eye and eyelid in cattle are generally referred to by the term "cancer eye". Approximately 80% of such tumors are malignant and many of the rest become malignant with time. Cancer eye is a serious problem throughout the United States, especially in high elevation locations where solar radiation is most intense. As pointed out by his article "Electrothermal treatment of Cancer Eye" by James D. Doss, published in the August 1977 issue of the *LASL Mini-Review*, 77-14, published in 1975 by the Los Alamos Scientific Laboratory of the University of California at Los Alamos, N. Mex., cancer eye was the leading individual cause of cattle carcass condemnation at slaughter houses inspected by the United States Department of Agriculture. In that year, losses due to cancer eye were though to exceed $20,000,000.00 per year in the United States alone. As a result of research at the above-mentioned Los Alamos Scientific Laboratory, techniques have been developed for on-range use involving passage of high frequency current through malignant tissue to increase its temperature to approximately 50° C. (122° F.) for thirty seconds, resulting in effective arresting of early discovered cases of cancer eye in cattle. Such temperature preferentially kills cancer cells, which are usually more susceptible to permanent damage by heat than healthy cells.

Several hand-held electrothermal devices have been developed which include high frequency oscillators that produce the needed high frequency current thorugh closely spaced probes that are pressed sufficiently hard against the malignant tissue to ensure good electrical contact thereto. In usual practice, the treatment of an animal with cancer eye involves the steps of restraining the animal, placing an eye spoon underneath and behind the eye ball to elevate and immobilize the eyeball. The electrodes of the electrothermal device then are held firmly against the surface of the tumor. The oscillator is activated, and high frequency current flows through the probes and the tissue and raises the temperature of the tissue, which in turn raises the temperature of the probe. When the temperature of the probe tip reaches the minimum required 50° C. temperature, the instrument emits periodic audible beeps every second, allowing the user to measure the amount of time adequate pressure of the electrodes is maintained against the surface of the tumor (for 30 seconds) by counting thirty beeps. A device manufactured by Veterinary Products Industries, of Phoenix, Ariz., referred to as the THERM-I-CURER LCF (localized current field) electronic probe, has been developed based on the above-mentioned research. This device produces an initial heat surge to a temperature of about 160° F. (60° C.) to 180° F. (68° C.) and then drops back to the sustained temperature of 50° C. for the required 30 second treatment. This initial surge is supposed to have a cauterizing effect that stops any bleeding, but, in fact, can cause undue permanent damage to healthy eye tissue.

The previous electrothermal devices and treatments, while representing a breakthrough in the treatment of cancer eye in cattle, nevertheless present certain unsolved problems. For example, the animal being treated usually vigorously resists attempts to restrain it, causing difficulty to the veterinary in maintaining adequate contact of the current probe contact surfaces with the tumorous tissue. But if adequate continuous electrical contact is not maintained during the entire treatment period, the temperature of the tissue may not reach or maintain the necessary temperature of 50° C. One of the previous electrothermal devices dissipates far too much power in the circuitry located in the handle of the device. Since it is frequently desirable to use the device at locations where electrical power is not available, it is highly desirable that the electrothermal devices be lightweight and battery-powered. This, of course, leads to the requirement that the electrothermal device not dissipate and waste excessive power. Another problem that sometimes occurs with prior art electrothermal devices is that the initial surge of current actually heats up tissue so rapidly that the temperature increase of the sensor (usually a thermistor) located in one of the probe tips lags the tissue temperature so that the circuitry cannot adequately regulate the amount of high frequency current applied to the tumor tissue before overheating of the tissue occurs. Such overheating can permanently damage healthy tissue which, of course, is highly undesirable.

Thus, there is an unmet need for an improved apparatus and method for electrothermal treatment of cancer eye in livestock. More specifically, there is a need for an improved electrothermal device and method which makes it easier for a veterinary to maintain sufficient pressure of the current probe contact surfaces against the cancer eye tissue to ensure adequate heating thereof despite any struggling by the animal.

There also is a need to provide such an electrothermal device and method that avoids excessive dissipation and waste of power.

There also is a need for such an electrothermal device that avoids excessive initial temperature overshoot or overheating of the cancer eye tissue.

Therefore, it is an object of the invention to provide an improved apparatus and method for electrothermal treatment of cancer eye or other tumorous tissue wherein a veterinary or other user is immediately and reliably alerted as to whether or not adequate pressure of the contact area of the current probes is being maintained against the cancer eye tissue or tumorous tissue.

It is another object of the invention to provide an apparatus and method for electrothermal treatment of cancer eye wherein the amount of wasted power dissipation is minimized.

It is another object of the invention to provide an apparatus and method for electrothermal treatment of cancer eye wherein the temperature of the cancer eye tissue is accurately maintained within a predetermined range during the treatment procedure.

It is another object of the invention to provide a device for electrothermal treatment of cancer eye wherein excessively rapid initial build-up of temperature in the cancer eye tissue is automatically avoided.

SUMMARY OF THE INVENTION

Briefly described and in accordance with one embodiment thereof, the invention provides a method and apparatus for accomplishing electrothermal treatment of malignant or tumorous tissue by providing an audible sound, the pitch of which represents the temperature of a high frequency current conducted by a pair of spaced probes which are held against the malignant or tumorous tissue. If the pressure of the contact surface of the high frequency current probes against the tissue is maintained at an adequate level, electrical contact also will be maintained, and the temperature of the tissue, and hence, of the probes steadily increases to a predetermined temperature due to a high frequency current flowing from one probe through the tissue and into the other probe. The probes are heated by thermal conduction of heat from the tissue to the probes. The steadily increasing pitch of the audible sound informs the user of the apparatus that sufficient pressure is being applied by the probe contact surfaces to the malignant tissue to provide the necessary degree of electrical contact between the probes and the tissue. In the event that the tissue is cancer eye tissue of a vigorously struggling animal, the pitch of the sound steadily increases as long as adequate probe pressure is maintained. This increasing pitch is helpful to the user in alerting him to any failure to maintain adequate probe pressure, so he can immediately correct the situation.

In the described embodiment of the invention, a thermistor disposed in one of the probe tips produces a signal which is amplified to produce a control voltage that represents the probe temperature. To the extent that the probe and the tissue are in thermal equilibrium, the control voltage represents the temperature of the tissue. The controlled voltage is coupled to a voltage controlled oscillator (VCO), a first timing circuit, and a duty cycle control circuit. The VCO circuit produces an audio frequency signal that is coupled to an audio transducer that produces the audible signal at the frequency of the audio frequency signal. The VCO circuit also produces a triangular output ramp voltage that is coupled to the duty cycle control circuit. The first timer circuit periodically modulates or interrupts the audio frequency signal as long as the temperature of the current probe exceeds approximately 50° C. This allows the user to "time" the duration of the period during which the malignant or tumorous tissue is maintained at or slightly above 50° C. by simply counting the number of audible beeps that are produced as a result of the modulation. The control voltage also is coupled to a circuit that generates a threshold voltage with which the instantaneous amplitude of the triangular ramp voltage is compared. As a result of this comparison, circuitry is provided which generates a duty cycle control signal. The duty cycle control signal interrupts a high frequency oscillator to control the "duty cycle" thereof from a high level when the temperature of the tissue is less than approximately 50° C. to a low level when the temperature of the tissue is above approximately 55° C. An integrating circuit integrates the duty cycle control signal. The resulting signal is compared with a signal that represents the temperature of the thermistor to adjust the threshold voltage with which the triangular ramp voltage is compared. During the initial eight seconds of operation, the circuit limits a duty cycle of approximately 50% on the high frequency oscillator to prevent temperature "overshoot" in the tissue, so that the temperature of the probe can rise nearly as rapidly as the temperature of the tissue being heated. After the eight seconds have elapsed, the duty cycle of the oscillator is controlled by the temperature of the thermistor in the current probe.

The two current probes are connected to the secondary winding of a transformer, the inputs of which are driven by two field effect transistors. The gate electrodes of the field effect transistors are driven by two buffered signals which are produced by the high frequency oscillator circuit; these two signals are 180° out of phase.

BRIEF DESCRIPTION OF THE DRAWINGS

FIG. 1 is a circuit schematic diagram of the circuitry of the invention.

FIG. 2 is a circuit schematic diagram of a ring oscillator used in the circuit of FIG. 1.

DESCRIPTION OF THE INVENTION

Figure 3:
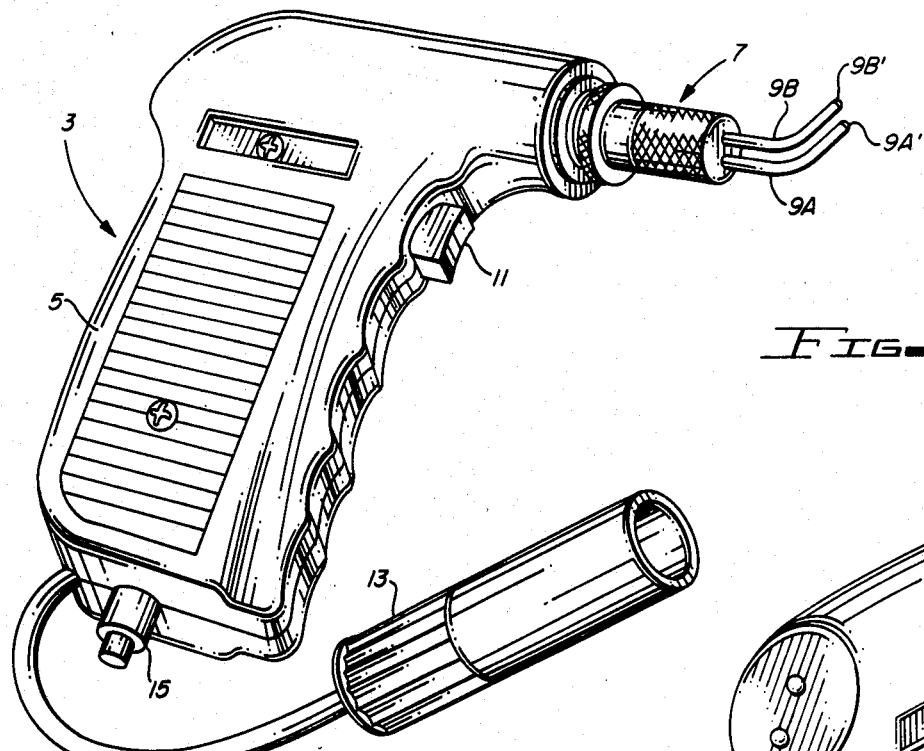
FIG. 3 is a perspective view of the electrothermal treatment apparatus in which the circuit of FIG. 1 is utilized.
Figure 3A:
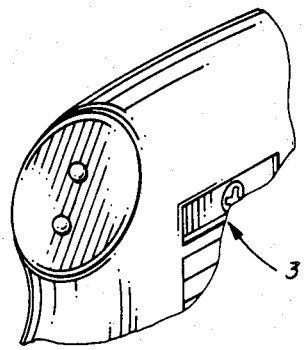
FIG.3A is a partial perspective view illustrating two indicator lights on the electrothermal apparatus shown in FIG. 3.

Referring now to the drawings, the circuit of FIG. 1 is positioned in the handle 5 of the electrothermal treatment apparatus 3 shown in FIG. 3. Apparatus 3 includes a momentary switch 11 which can be actuated by the index finger of a person gripping handle 5 to actuate circuit 1. When circuit 1 is actuated, a high frequency (approximately 2 Mhz) output voltage produced thereby appears across two spaced, electrically conductive electrically isolated probes 9A and 9B. If probes 9A and 9B are held against cancerous tissue in the eye of a livestock animal with adequate pressure, the resulting contact resistances will be sufficiently low that voltage between probes 9A and 9B causes a high frequency current to flow from one of the probes through the cancerous tissue into the other. This causes resistive heating of the cancerous tissue. As previously explained, the technique of treating "cancer eye" in cattle has been proven to be quite effective.

Reference numeral 15 of FIG. 3 designates a main switch that makes power supplied via an electrical connector 13 available to circuit 1 on conductor 21.

Referring now to FIG. 1, the structure of circuit 1 will be set forth in detail. Thermistor 17, which is located in the tip of one of probes 9A and 9B, is connected between ground conductor 18 and conductor 19. The purpose of thermistor 17 is to determine the temperature to which the cancerous tissue has been raised. Thermistor 17 is connected in series with resistor 20, the upward end of which is connected to a supply voltage conductor 21 that has a potential of +V volts. Actuation of switch 11 applies the voltage $V_{in}$ to conductor 21 to actuate circuit 1. ($V_{in}$ is made available by means of switch 15 of FIG. 3).

The voltage on conductor 19 is applied by means of a resistor 22B to the positive input of operational amplifier 22. Resistors 23 and 24 are connected in series between +V and ground to produce a reference voltage on conductor 25. The voltage on conductor 25 is applied by a resistor 22A to the negative input of operational amplifier 22, so that when the voltage on conductor 19 exceeds the reference voltage on conductor 25, the output of operational amplifier 22 goes to a high level. (Note that operational amplifiers 22, 26, 40 and 46 of FIG. 1 can be implemented by means of an LM324N integrated circuit quad operational amplifier.)

The output of operational amplifier 22 is connected to the negative input of operational amplifier 26. The positive input of operational amplifier 26 is connected to the junction between resistors 27 and 29, which are connected in series between +V and ground to establish a switching point for operational amplifier 26 that corresponds to a thermistor temperature of 50° C.

The output of operational amplifier 26 is coupled to the base of NPN transistor 30, the collector of which is connected to +V, its emitter being connected to conductor 31. Conductor 31 is connected to the reset input of a "555" integrated circuit timer, which is widely available. The 555 timer is designated by reference numeral 32, and is connected as shown to provide a two second oscillation frequency at its output on conductor 33. When momentary switch 11 is held closed, the output of timer 32 is connected to one input of a ceramic transducer 34, which functions as an audio frequency speaker. Conductor 33 serves as a "ground return" line for transducer 34, the other terminal of which is coupled by capacitor 35 to conductor 36, to which an audio frequency signal proportional in magnitude to the temperature of thermistor 17 is applied, as subsequently explained.

Light emitting diode 37 is also connected to conductor 33, and blinks in synchronization with oscillation of timer 32 at a two second repetition rate.

The output of operational amplifier 22 produces an amplified voltage on conductor 38 proportional to the temperature of thermistor 17. This voltage is applied to the input of a voltage controlled oscillator (VCO) circuit 39. VCO circuit 39 includes operational amplifier 40, the negative input of which is connected by resistor 41 to conductor 38. Resistor 42 connects the output of operational amplifier 40 back to the negative input thereof.

The positive input of operational amplifier 40 is connected to conductor 43 which, in turn, is connected to the junction between resistors 44 and 45. Resistors 44 and 45 are connected in series between +V and ground. The positive of input of operational amplifier 46 is connected by resistor 47 to conductor 43 and is also connected to the junction 48 between the cathode of diode 49 and the anode of diode 50. The output of operational amplifier 46 is connected by resistor 51 to conductor 52, which is one of the outputs of VCO circuit 39. The anode of diode 49 is connected by resistor 53 to the output of operational amplifier 40. The cathode of diode 50 is connected by resistor 54 to conductor 38. Conductor 48 is connected by resistor 55 to conductor 52.

The negative input of operational amplifier 46 is connected to conductor 56, which is a second output of VCO circuit 39. Conductor 56 is connected by resistor 57 to conductor 52 and also is connected by capacitor 58 to conductor 43.

Those skilled in the art will realize the VCO circuit 39 produces a triangular waveform signal on conductor 56 and a square wave signal on conductor 52, and that the frequency on both such waveforms is proportional to the voltage on conductor 38, and hence to the temperature of thermistor 17.

The square wave signal on conductor 52 is applied to the base of NPN transistor 59, the collector of which is connected to +V and the emitter of which is connected to conductor 36 to thereby apply an audio frequency signal to one input of audio transducer 34. Thus, it is seen that the pitch of the sound emitted by audio transducer 34 is proportional to the temperature of transducer 17.

The triangular waveshape produced on conductor 56 is applied to the negative input of operational amplifier 60, which functions as a comparator in this case. (Note that operational amplifiers 60, 79, 87 and 92 also can be implemented by means of LM324N integrated circuit quad op amps. Note also that the op amps can be connected to function as comparators.) The triangular waveform on conductor 56 is compared with the DC voltage on conductor 61, which is connected to the positive input of comparator 60 to establish the switching point of comparator 60. The output of comparator 60 is connected to conductor 62, which is coupled by resistor 63 to the base of NPN transistor 64. The base of transistor 64 is connected by resistor 65 to ground. The emitter of transistor 64 is connected to ground, and the collector is connected to a duty cycle control input of a ring oscillator circuit 66.

As subsequently explained with reference to FIG. 2, oscillator 66 is set to oscillate at approximately 2 megahertz. It has a duty cycle control input connected to conductor 67 which halts the oscillation when that input is at a logical "0". Conductor 67 is connected to the collector of transistor 64. The signal produced on conductor 67 in effect modulates the "duty cycle" of the two megahertz bursts produced on output conductors 68 and 69 of ring oscillator circuit 66. Conductor 68 is connected to the input of an inverter-driver circuit 70, the output of which is connected to the gate electrode of a VMOS power field effect transistor 71. The source electrode of VMOS transistor 71 is connected to ground, and its drain electrode is connected to one primary terminal of transformer 72. Conductor 69 is connected to the input of inverter-driver 73, the output of which is connected to the gate electrode of VMOS power transistor 74. The source electrode of transistor 74 is connected to ground and its drain electrode is connected to the other primary winding terminal of transformer 72.

A center tap electrode 75 of the primary winding of transformer 72 is coupled by inductor 76 to +V conductor 21. Capacitor 78 is connected between center tap 75 and ground. The terminals of the secondary winding of transformer 72 are connected by conductors 77A and 77B to probes 9A and 9B, respectively, of electrothermal apparatus 3 of FIG. 3.

Circuitry 102 performs the function of regulating the duty cycle control signal applied to oscillator 66 to maintain the temperature of the cancerous or tumerous tissue in the range between 50° C. and 55° C. The threshold level applied by conductor 61 to the positive input of comparator 60 normally represents the temperature of thermistor 17 in the range from 50° C. to 55° C., so that the "duty cycle" of the two megahertz voltage applied to probes 9A and 9B is automatically varied to keep it in the range between 50° and 55° C. To accomplish this, operational amplifier 79 has its output connected by conductor 61 to the negative input of comparator 60. The negative input of comparator 79 is connected by means of capacitor 80 to conductor 61. The negative input of comparator 79 also is connected to conductor 81, which is connected to the junction between resistors 82 and 83. Resistors 82 and 83 are connected in series between +V and ground. Conductor 81 is also connected to the junction between resistor 84 and capacitor 85, the other terminal of resistor 84 being connected to conductor 62 and the other terminal of capacitor 85 being connected to ground.

The positive input of operational amplifier 79 is connected to conductor 86.

Conductor 38, previously referred to, is connected by resistor 87A to the input of operational amplifier 87. The positive input of operational amplifier 87 is connected to the junction between resistors 88 and 89, which are connected in series between +V and ground. The output of operational amplifier 87 is connected by resistor 90 to conductor 86 and by resistor 91 to the negative input thereof.

The immediately foregoing circuitry performs a "scaling" function on the voltage produced in response to thermistor 17 by operational amplifier 22 in order to produce a scaled voltage representative of the temperature of thermistor 17 in the range from 50° to 55° C. on conductor 86.

Circuitry 106 performs the function of causing circuitry 102 to impose a reduced "duty cycle" of approximately 50% on the duty cycle control signal applied to oscillator 66 for the first 8 seconds that power is applied to circuit 1. Reference numeral 92 designates a comparator having its positive input connected to the junction between resistors 93 and 94, which are connected in series between +V and ground to establish a reference voltage equal to approximately two-thirds of the value of +V. The negative input of amplifier comparator 92 is connected to the junction between resistor 95 and capacitor 96, which are connected in series between +V and ground to produce a slowly rising signal when +V volts is applied to conductor 21 in response to closing of switch 11. The output of comparator 92 is coupled by resistor 97 to the anode of diode 98, the cathode of which is connected to conductor 86. The immediately foregoing circuit cooperates with circuitry 102 to limit the "duty cycle" of oscillator 66 to approximately 50% for the first eight seconds after switch 11 is actuated. For the first eight seconds, comparator 92 produces a high output voltage by forward biasing diode 98 and establishes a switchpoint at the positive input of comparator 79. This switchpoint voltage is determined by the value of resistors 97 and 92A and by the forward voltage drop of diode 98.

The operation of circuit 1 will now be explained with reference to the waveforms of FIG. 4.

First, after immobilizing the animal's eye by means of a spoon which is inserted behind the eyeball, the user holds the electrothermal treatment apparatus 3 of FIG. 3 in his hand and presses the lower probe contact surfaces 9A' and 9B' (FIG. 3) against the cancerous tissue and then depresses momentary switch 11. This closes the two switch "wiper" elements designated by reference numeral 11 in FIG. 1 and applies +V volts to conductor 21 of circuit 1. (It is assumed that switch 15 has been closed, making the voltage $V_{in}$ available to circuit 1). It should be borne in mind that the animal may be struggling and that the user may experience considerable difficulty in maintaining contact surfaces 9A' and 9B' against the cancer eye tissue with a sufficient amount of pressure to ensure adequate electrical contact. Obviously, if inadequate contact of areas 9A' and 9B' against the cancerous tissue is maintained, this will increase the impedance load on the output of circuit 1. The increased impedance will decrease the amount of two megahertz current flowing through probes 9A and 9B and the cancerous tissue, preventing its temperature from being raised to an adequate level.

With this in mind, it will be recognized that if adequate probe contact pressure is maintained against the cancerous tissue, the temperature of the tissue will begin to rise quite rapidly. As the temperature of the tissue rises, the temperatures of probes 9A and 9B also rise, although with a slight lag in time which may vary from a fraction of a second to more than one second. The temperature of thermistor 17 is almost exactly equal to the temperature of the one of probes 9A and 9B in which it is disposed. The circuit within block 99 amplifies the voltage across thermistor 17, producing a voltage on conductor 38 which is proportional to the thermistor temperature. When the thermistor temperature reaches approximately 50° C., the voltage on conductor 38 exceeds the threshold voltage applied to the positive input of comparator 26. Comparator 26 then switches, causing transistor 30 to apply an enable input to timer 32, enabling it to function as an astable multi-vibrator with a two second period on its output 33.

Meanwhile, as soon as the temperature of thermistor 17 begins to increase, the voltage on conductor 38 also begins to increase, and VCO circuit 39 begins to oscillate at an audio frequency that increases at a rate that is proportional to the increase in the voltage on conductor 38. VCO circuit 39 produces a square wave signal on conductor 36 which is applied via capacitor 35 to one terminal of audio transducer 34. Until timer 32 begins switching at its two second repetition rate, the voltage on conductor 33 is at +V. (Switch 11, of course, is closed.) The square wave produced on conductor 36 is smoothed somewhat by capacitor 35 and resistor 35', producing a relatively pure sinusoidal waveform of gradually increasing pitch across transducer 34, causing an audible sound of increasing pitch to be emitted by transducer 34. The range of audio frequencies of the sound is roughly 1 kilohertz to 4 kilohertz.

The user of electrothermal apparatus 3 knows that as long as the pitch of the sound emitted by transducer 34 continues to increase at a proper rate, he is maintaining adequate pressure of contact surfaces 9A' and 9B' against the cancerous tissue because its temperature is increasing at the same rate as the pitch of the sound emitted by transducer 34. If adequate contact is momentarily lost due, for example, to the struggling of the animal, the user realizes this immediately, because the pitch of the sound emitted by transducer 34 immediately stops increasing, and may, in fact, begin decreasing if the temperature of thermistor 17 begins to fall sharply due to loss of adequate probe surface contact with the cancerous tissue.

When adequate pressure of the probe contact surface has been maintained with the cancerous tissue for a sufficiently long period of time (typically approximately 10 seconds) the temperature of thermistor 17 will reach 50° C., and the voltage on conductor 33 produced by timer 32 will begin to rise and fall with a two second repetition rate, thereby periodically interrupting the ground return connection of ceramic transducer 34, so that the sound emitted thereby beeps at a two second repetition rate. As long as the temperature of the tissue is at least 50° C., the beeping will continue and the user can count the number of beeps until 15 of them have occurred, indicating that the cancerous tissue has been held at least 50° C. for at least 30 seconds. At this point, the probes can be removed and switch 11 can be released.

The circuit of FIG. 1 automatically regulates the temperature of the cancerous tissue, i.e., of thermistor 17, by modulating the "duty cycle" of the two megahertz current conducted via probes 9A and 9B to the cancerous tissue. To understand how this is done, it must be realized that ring oscillator 66 produces two non-overlapping square wave signals on conductor 68 and 69. These square wave signals are buffered by driver circuits 70 and 73, respectively, which alternately turn VMOS power transistors 71 and 74 on and off in such a manner that at no time are both transistor 71 and 74 on simultaneously. (Note that VMOS power transistors 71 and 74 can be the IRF523 or higher voltage IRF522 VMOS transistors manufactured by International Rectifier Corporation). The repetition rate of the switching of each of power transistors 71 and 74 is approximately two megahertz. After the temperature of thermistor 17 rises to approximately 50° C., the modulation signal produced on conductor 67 varies the "duty cycle" of the two megahertz "burst" applied to the primary winding of transformer 72 to keep the temperature of thermistor 17 in the range from 50° C. to 55° C. In FIG. 4, waveform 100 illustrates the bursts of two megahertz current applied through probes 9A and 9B at a relatively high "duty cycle" corresponding to a thermistor temperature at the low end of the range from 50° C. to 55° C., whereas waveform 101 represents a relatively low duty cycle of the bursts of two megahertz current that would be produced by the automatic duty cycle regulating circuit represented by reference numeral 102 in FIG. 1 for a thermistor temperature at the high end of the range from 50° C. to 55° C. It is to be understood that the term "duty cycle" as used herein refers to the duty cycle of the "envelope" of the bursts of 2 MHz current, and not to each individual cycle of the 2 MHz current. However, the true duty cycle of each cycle of the 2 MHz current also culd be varied to regulate the power delivered to the cancerous tissue.

Figure 4:
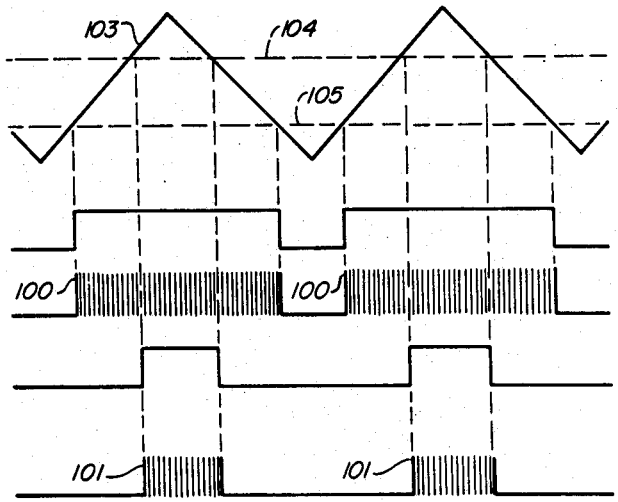
FIG. 4 is a diagram of several waveforms that are useful in illustrating the operation of the circuit of FIG. 1.

In FIG. 4, reference numeral 103 represents the above-mentioned triangular waveform produced by VCO circuit 39 on conductor 56. Dotted line 104 represents a relatively high threshold or trip point of comparator 79, applied as a voltage on conductor 86 for a relatively high thermistor temperature near 55° C. When the voltage on conductor 56 is above the voltage represented by dotted line 104 the output of comparator 60 produces a signal that drives transistor 64 and starts two megahertz oscillator circuit 66, resulting in the two megahertz burst of pulses represented by reference numeral 101; this burst lasts as long as the triangular wave shape 103 is above threshold 104. As an alternate example, if the thermistor temperature is at the low end of the range from 50° C. to 55° C., a higher "duty cycle" of the current bursts is needed to pump more two megahertz current into the cancerous tissue, and a lower threshold voltage will appear on conductor 86. This lower threshold voltage is represented by dotted line 105 in FIG. 4, and comparator 60 functions as described above to produce wider bursts of two megahertz current, such as the ones indicated by reference numeral 100 in FIG. 4.

As previously mentioned, under certain circumstances, the thermal lag in the temperature of the probe in which thermistor 17 is disposed relative to the rapidly rising temperature of the cancerous tissue during the initial period immediately after switch 11 is closed can result in temperature "over-shoot" of the cancerous tissue to the extent that healthy eye tissue may be damaged. In order to prevent this occurrence, the invention provides the above-mentioned automatic initial eight second period in which the duty cycle of the two megahertz current is limited to 50% for the first eight seconds of operation. This ensures that the temperature of thermistor 17 rises nearly as fast as the temperature of the cancerous tissue, thereby ensuring that the temperature sensed by thermistor 17 accurately represents the temperature of the cancerous tissue. The circuitry designated by reference numeral 106 in FIG. 1 operates to produce a slowly rising waveform that is applied to the negative input of comparator 92, beginning at the instant that switch 11 is closed. Current through resistor 95 charges up capacitor 96 to produce this signal which, when it equals a voltage of approximately two thirds of +V (which typically is approximately 8 volts), causes the output of comparator 92 to fall and go to zero volts. This reverse biases diode 98, allowing the voltage on conductor 86 to be determined by operational amplifier 87, which scales the temperature sensitive voltage produced by thermistor sensing circuit 99. Therefore, after the eight second delay time has elapsed, circuit 1 functions as previously described. However, during that initial eight second time period, the output of comparator 92 is high, diode 98 is forward biased, thereby maintaining the positive input of comparator 79 in circuitry 102 at the above-mentioned relatively high level.

The operation of the duty cycle regulating circuit generally designated by reference numeral 102 in FIG. 1 is as follows. First, comparator 60 compares the triangular waveform 103 (FIG. 4) with the output of operational amplifier 79, which is produced on conductor 61. The positive input of operational amplifier 79 is connected to conductor 86. (Recall that the voltage on conductor 86 is equal to the voltage at the junction between resistors 97 and 92A in circuit 106 for approximately the first eight seconds of operation to force the duty cycle to be approximately 50%. After the first eight seconds of operation have elapsed, the voltage on conductor 86 is a scaled down voltage that is proportional to the temperature of thermistor 17.)

In either case, the voltage on conductor 86 is compared with the voltage on conductor 81 in duty cycle regulating circuit 102, since the latter voltage is applied to the negative input of operational amplifier 79, as operational amplifier 79 actually functions as a comparator in this circuit.

The circuitry including resistor 84, capacitor 85, operational amplifier 79 and capacitor 80 functions as an integrator which averages the voltage signal on conductor 62. If the temperature of thermistor 17 is above 50° C., or during the first eight seconds of operation, the voltage on conductor 62 will be a sequence of pulses, the duty cycle of which depends on the voltage on conductor 86. After the first eight seconds of operation, but before the temperature of thermistor 17 attains 50° C., the voltage on conductor 62 will be a logical "1", rather than a sequence of pulses. During this time, the voltage on conductor 81 is equal to the voltage on conductor 62. Operational amplifier 79 compares the voltage on conductor 81 with the voltage conductor on 86, and forces the voltage on conductor 61 to be +V. That causes comparator 60 to force the voltage on conductor 62 to equal +V (i.e., to have a 100% duty cycle). However, once the duty cycle of the voltage produced on conductor 62 becomes less than 100%, (i.e., after the temperature of thermistor 17 exceeds 50° C.) then the above-mentioned integrating circuit averages that value. Then the operation of the duty cycle regulating circuit 102 is as follows. Operational amplifier 79 compares the average of the duty cycle voltage on conductor 62 with the voltage on conductor 86. Then operational amplifier 79 sets the threshold on conductor 61 such that comparator 60 forces the average voltage on conductor 62 to be equal to the present reference voltage on conductor 86. This operation results in linear reduction of the duty cycle of the signal on conductor 62, and hence, on conductor 67, with respect to increasing temperature of thermistor 17 from approximately 50° C. to approximately 55° C.

The details of ring oscillator circuit 66 can be described with reference to FIG. 2, wherein it can be seen that the major components of ring oscillator 66 include two one-shot integrated circuits 107 and 108 (each of which can be implemented by means of 74123N integrated circuits.) They can be interconnected in the manner shown with resistors 109, 110, and 112 and capacitors 111 and 113 selected to produce a two megahertz oscillation frequency. This circuit is well known to those skilled in the art, and its operation need not be described, except to note that it produces two out-of-phase, two megahertz square wave signals on conductors 68 and 69 whenever conductor 67 is held high.

An important advantage of the circuit described in FIG. 1 relates to the use of high power VMOS transistors 71 and 74 to drive the primary winding of transformer 72. In the past, oscillator circuits used in electrothermal apparatus for treatment of eye cancer have utilized a NPN bipolar transistor in a Collpitts oscillator or a Hartley oscillator to generate the two megahertz frequency. The bipolar power transistor of such circuits is always at least slightly on, and therefore continuously conducts current. The highest magnitude of current occurs when the transistor is saturated, and a very large amount of power is dissipated as a result of this current flowing across the $V_{sat}$ voltage drop between the collector and the emitter of the bipolar NPN transistor. This has resulted in excessive waste of power. It is highly desirable that the electrothermal treatment apparatus used for treating eye cancer in cattle be both portable and battery powered. The excess waste of power of the prior device reduces the number of treatments that can be performed before the batteries need to be re-charged; the excessive power dissipation has also resulted in the handle of some prior devices becoming excessively hot.

The device of FIG. 3, utilizing the circuit of FIG. 1 therein, completely avoids these problems, and is capable of delivering over 90% of the power supplied from the battery through the probes 9A and 9B to the cancerous tissue, if VMOS transistors having sufficiently low channel resistance are used. This occurs because the channel resistance of VMOS devices 71 and 74 is very low, less than a fraction of an ohm, and MOS transistors inherently have no $V_{sat}$ voltage across which the excessive power dissipation of prior devices occurs. The use of essentially square wave current waveforms, which is what are produced by VMOS transistors 71 and 74 and transformer 72, results in high harmonic frequency content of the current passing through the tissue. It is thought, although it has not yet been proved, that this may result in improved heating of the tissue.

While the invention has been described with reference to a particular embodiment thereof, those skilled in the art will be able to make various modifications without departing from the true spirit and scope of the invention. It is intended that all apparatus and methods which are substantially equivalent to those disclosed and claimed herein in that they perform substantially the same function in substantially the same way to obtain substantially the same result be encompassed within the scope of the invention. For example, since the pitch of the audible sound represents the temperature of the tissue, the rate of increase of the pitch can also indicate if the rf power being supplied to the probes is adequate to heat the tissue being contacted by the probe. An improved embodiment of the invention is contemplated wherein the power output level of the $V_{MOS}$ transistors 71 and 74 and transformer 72 is adjustable by the user. This would be important in instances wherein the electrothermal device would be used for treatment of a wide range of sizes of tumerous tissue. More power would obviously be required for larger tumors. If too low a power setting were used for a large tumor, failure of the pitch of the audible sound to increase at a predetermined rate despite adequate probe pressure being maintained would alert the user that the power level should be increased. Although the described embodiment of the invention requires the user to count the number of audible beeps to ensure that the tumerous tissue has been maintained at an adequately high temperature for an adequately long time initially, it would be quite feasible to add timing circuitry to count and display the number of seconds that the tissue has been held above a predetermined temperature such as 50° C. Although the described embodiment of the invention provides a 50% duty cycle for the first eight seconds to avoid temperature overshoots, it would be quite feasible to use some other approach, such as gradually increasing the duty cycle from an initial low level to high level. Although various government regulations must be complied with for apparatus and methods used for human medical treatment, it is believed that the described embodiment of the invention can be modified to effectively treat certain skin growths, such as warts, in humans.

I claim:

1. In an apparatus for electrothermal treatment of unhealthy tissue, a circuit for producing a flow of a high frequency current through the unhealthy tissue to heat it without damaging adjacent healthy tissue, said electrothermal apparatus including first and second spaced current probes each having a contact surface for electrically contacting the surface of said unhealthy tissue to thereby conduct said high frequency current through said unhealthy tissue, said electrothermal treatment apparatus also including output oscillating circuit means for producing a high frequency voltage signal for application across said first and second current probes to cause said high frequency current to flow through said unhealthy tissue if said contact surfaces are held sufficiently forcefully against the surface of said unhealthy tissue, said output oscillating circuit means including a control input for receiving a duty cycle signal for regulating the duty cycle of the flow of high frequency current, said circuit comprising in combination:

(a) temperature sensing means for sensing the temperature of said first current probe to produce a first electrical signal representative of the temperature of said first probe, the temperature of said first current probe being indicative of the temperature of said unhealthy tissue and hence the amount of said high frequency current flowing through said unhealthy tissue, the amount of said high frequency current flowing through said unhealthy tissue being dependent upon the contact resistance between said unhealthy tissue and said first and second current probes, said contact resistance between said unhealthy tissue and said first and second current probes being dependent upon the force with which said first and second current probes are held against said unhealthy tissue;

(b) voltage controlled oscillating circuit means responsive to said first electrical signal for producing an audio signal representative of the temperature of said first current probe and indicative of the sufficiency the forces pressing said contact surfaces of first and second current probes against said unhealthy tissue;

(c) audio transducer means responsive to said audio sound for producing an audible sound, the pitch of which represents the temperature of said first current probe and hence the temperature of said unhealthy tissue, the rate of change of the pitch being indicative of said sufficiency of said forces when said unhealthy tissue is being heated by said high frequency current;

(d) regulating circuit means for generating said duty cycle signal for application to said control input of said oscillating circuit means; and (e) delay circuit means for reducing the duty cycle of said high frequency current to a predetermined level for a predetermined initial time period after initial application of operating power to said circuit, to prevent initial overheating of said tissue due to thermal lag between heating of said unhealthy tissue by said high frequency current and heating of said first current probe by themal conduction of heat thereto from said unhealthy tissue;

whereby the user of said electrothermal treatment apparatus can be immediately notified of a condition of insufficient contact surface pressure of the either of said first and second current probes against said unhealthy tissue by a predetermined change in the pitch of said audible sound and can thereby immediately increase the contact surface pressure.

2. In an apparatus for electrothermal treatment of unhealthy tissue, a circuit for producing a flow of a high frequency current through the unhealthy tissue to heat it without damaging adjacent healthy tissue, said electrothermal apparatus including first and second spaced current probes each having a contact surface for electrically contacting the surface of said unhealthy tissue to thereby conduct said high frequency electrical current through said unhealthy tissue, said electrothermal treatment apparatus also including output oscillating circuit means for producing a high frequency voltage signal for application across said first and second current probes to cause said high frequency current to flow through said unhealthy tissue if said contact surfaces are held sufficiently forcefully against the surface of said unhealthy tissue, said output oscillating circuit means including a control input,
said circuit comprising in combination:

(a) temperature sensing means for sensing the temperature of said first current probe to produce a first electrical signal representative of the temperature of said first probe;

(b) delay circuit means for reducing the duty cycle of said high frequency current to a predetermined level for a predetermined initial time period after initial application of operating power to said circuit, to prevent initial overheating of said tissue due to thermal lag between heating of said unhealthy tissue by said high frequency current and heating of said first current probe by thermal conduction of heat thereto from said unhealthy tissue;

(c) means responsive to said control input for halting oscillation of said output oscillating circuit means when said control input is at a first signal level; and (d) regulating circuit means responsive to said first electrical signal and coupled to so said control input means for periodically interrupting oscillating of said output oscillating circuit means after said predetermined initial time period in order to reduce a duty cycle of said high frequency current and thereby reduce the amount of heating of said unhealthy tissue by said high frequency current.

3. A method of operating an apparatus to electrothermally treat unhealthy tissue by conducting high frequency current through first and second current probes and through said unhealthy tissue to cause heating of said unhealthy tissue to at least a first predetermined temperature for at least a predetermined amount of time in order to kill said unhealthy tissue without causing undue damage to adjacent healthy tissue, said method comprising the steps of:

(a) pressing each of said first and second current probes against the surface of said unhealthy tissue with sufficient force to reduce the contact resistance between said first and second probes and said unhealthy tissue to a level that enables a predetermined amount of said high frequency current to flow through the unhealthy tissue disposed between said first and second current probes;

(b) applying electrical power to a circuit that produces a high frequency voltage across said first and second current probes to cause said high frequency current to flow, the voltage and current being at a particular duty cycle;

(c) conducting said high frequency current from one of said first and second current probes through said unhealthy tissue between said first and second current probes to the other of said first and second current probes to cause heating of that unhealthy tissue, heat from said unhealthy tissue flowing by thermal conduction to said first current probe and raising the temperature thereof, the temperature of said first current probe being indicative of the temperature of said unhealthy tissue and hence the amount of said high frequency current flowing through said unhealthy tissue, the amount of said high frequency current flowing through said unhealthy tissue being dependent upon the contact resistance between said unhealthy tissue and said first and second current probes, said contact resistance between said unhealthy tissue and said first and second current probes being dependent upon the force with which said first and second current probes are held against said unhealthy tissue;

(d) sensing the temperature of said first probe to produce a first electrical signal;

(e) producing an audio frequency signal representative of the temperature of said first current probe and indicative of said sufficieny of said forces, and applying said audio frequency signal to an audio frequency sound transducer which produces an audible sound, the pitch of which is presentative of the temperature of said first current probe, and the rate of change of said pitch being indicative of said sufficiency of said forces, the pitch of said sound gradually increasing and informing a person operating said apparatus whether that person is applying adequate pressure on both of said first and second current probes to cause adequate electrical current to flow through said first and second current probes and said unhealthy tissue to raise the temperature thereof at a satisfactory rate; and (f) limiting the duty cycle of said high frequency voltage and said high frequency current to a predetermined duty cycle for a predetermined amount of time after the beginning of said conducting of said high frequency current through said unhealthy tissue, said predetermined duty cycle having a value which prevents initial heating of said unhealthy tissue at a rate that excessively exceeds the rate of thermal conductive heating of said first probe by the heated unhealthy tissue.

4. In an apparatus for electrothermal treatment of unhealthy tissue, a circuit for producing a flow of high frequency current through the unhealthy tissue to heat it without damaging adjacent healthy tissue, said electrothermal apparatus including first and second spaced current probes each having a contact surface for electrically contacting the surface of said unhealthy tissue to thereby conduct said high frequency electrical current through said unhealthy tissue, said electrothermal treatment apparatus also including output oscillating circuit means for producing a high frequency voltage signal for application across said first and second current probes to cause said high frequency current to flow through said unhealthy tissue if said contact surfaces are held sufficiently forcefully against the surface of said unhealthy tissue, said circuit comprising in combination:

(a) temperature sensing means for sensing the temperature of said first current probe to produce a first electrical signal representative of the temperature of said first probe, the temperature of said first current probe being indicative of the temperature of said unhealthy tissue and hence the amount of said high frequency current flowing through said unhealthy tissue, the amount of said high frequency current flowing through said unhealthy tissue being dependent upon the contact resistance between said unhealthy tissue and said first and second current probes, said contact resistance between said unhealthy tissue and said first and second current probes being dependent upon the force with which said first and second current probes are held against said unhealthy tissue;

(b) voltage controlled oscillating circuit means responsive to said first electrical signal for producing an audio signal representative of the temperature of said first current probe and indicative of the sufficiency of the forces pressing said contact surfaces of first and second current probes against said unhealthy tissue;

(c) audio transducer means responsive to said audio signal for producing an audible sound, the pitch of which represents the temperature of said first current probe and hence the temperature of said unhealthy tissue, the rate of change of the pitch being indicative of said sufficiency of said forces when said unhealthy tissue is being heated by said high frequency current; and whereby the user of said electrothermal treatment apparatus can be immediately notified of a condition of insufficient contact surface pressure of the other of said first and second current probes against said unhealthy tissue by a predetermined change in the pitch of said audible sound and can thereby immediately increase the contact surface pressure.

* * * * *